US006869601B2

United States Patent
Goel et al.

(10) Patent No.: US 6,869,601 B2
(45) Date of Patent: Mar. 22, 2005

(54) BACTERIAL MUTANT BX065 AND A METHOD THEREOF

(75) Inventors: Ajay Kumar Goel, Hyderabad (IN); Lakshmi Rajagopal, Hyderabad (IN); Ramesh V Sonti, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 38 days.

(21) Appl. No.: 10/109,574

(22) Filed: Mar. 27, 2002

(65) Prior Publication Data

US 2003/0003078 A1 Jan. 2, 2003

Related U.S. Application Data (60) Provisional application No. 60/279,921, filed on Mar. 29, 2001.

(51) Int. Cl.[7] .................... A01N 63/00; A01N 65/00; C12N 15/00; C12N 15/01; C12N 1/00
(52) U.S. Cl. ............... 424/93.4; 424/93.1; 435/440; 435/441; 435/243; 435/252.1
(58) Field of Search ............... 435/440, 441, 435/243, 252.1; 424/93.1, 93.4

(56) References Cited

PUBLICATIONS

Rajagopal et al, FEBS Letters, 1997, 415:125–128.*
Rajeshwari et al, J. Bacteriology, Sep. 2000, 182/17:4797–4802.*
Rajeshwari et al, Can. J. Microbiol., 1997, 43:862–867.*
Tsuchiya et al, Genetics, 1982, 72/1:43–46.*
Dharmapuri et al, FEMS Microbiology Letters, 1999, 179:53–59.*
Goel et al, Applied and Environmental Microbiology, Jan. 2001, 67/1:245–250.*
Ray et al, Molecular Plant–Microbe Interactions, 2000, 13/4:394–401.*
Dardick et al, Genetics and Resistance, 2003, 93:705–711.*
Dharmapuri et al, Molecular Plant–Microbe Interactions, 2001, 14/11:1335–1339.*
Anton et al, Biochem. J. 1988, 249:319–326.*
Sun et al, FEMS Micrbiology Letters, 2003, 226:145–150.*
Shen et al, Microbes and Infection, 2002, 4:1361–1367.*
Chatterjee et al, MPMI, 2003, 16/11:973–982.*
Kumar et al, Current Microbiology, 2003, 46:251–255.*
Chatterjee et al, MPMI, 2002, 15/5:463–471.*
Futamura et al, J. Bioscience and Bioengineering, 2001, 91/3:272–276.*
Padmavati et al, Phytochemistry, 1997, 46/3:499–502.*
Nakai et al, Sabrao Journal, 1975, 7/2:159–170.*
Taura et al, Japan J. Breed, 1991, 41:279–288.*
Nayak et al, II Riso, 1978,, 27/4:311–316.*
Kelemu et al, Molecular Plant–Microbe Interactions, 1990, 3/2:59–65.*
Lim et al, FEMS Microbiology Letters, 2004, 238:101–106.*
Whipp et al, Gene, 1998, 209:185–192.*
Bai et al, MPMI, 2000, 13/12:1322–1329.*
White et al, Current Opinion in Plant Biology, 2000, 3:291–298.*

* cited by examiner

Primary Examiner—N. M. Minnifield
(74) Attorney, Agent, or Firm—Merchant & Gould P.C.

(57) ABSTRACT

The present invention relates to a mutant bacteria *Xanthomonas oryzae* pathovar oryzae BXO65 with mutation at a site coding for enzyme shikimate dehydrogenase and a method of producing said mutant and also a method of

```
     EcoRI
  1  GAATTCAGCAGCAAGCCCGAAGCAGACGGGACGCAGAGTAGACTTGCCGCCAGCGTGAGCAGCCCATCGATAGTGCATGCGGTGTTCCTGCCTCAAGTCGC    100
                                                      S/D                      -35                    -10                aroE3
101  GCACAGTCTAGTCAACCAGAGAGCGTTTCATGCCCGTATCCCGTTATGCGGTCGGTGTTCGGTCACCCGTCGCCCATTCCCTGTCGCCGGCTATCCATGCCGA    200
                                                      M  P  V  S  R  Y  A  V  F  G  H  P  V  A  H  S  L  S  P  A  I  H  A  D     24
201  CTTCGGGAAGCAGACGCATTGTGCTGGACTACACCGCGATCGATGCCCCGCCAGAGGACTTCAGTGCCGCGCTGCAAGCGTTCGCCGGATGGAGGCGGC    300
      F  G  K  Q  T  G  I  V  L  D  Y  T  A  I  D  A  P  P  E  D  F  S  A  A  L  Q  R  F  A  D  G  G  G     57
301  AAGGGTGCGAACGTCACCCTGCCGTTGAAAGAAGCGGCCTGTGCCGCCCTGGCCAGTAGCCTCAGCGATCGGGCGCGGCTGGCAGGGGTGAACACCCTGG    400
      K  G  A  N  V  T  L  P  L  K  E  A  A  C  A  L  A  S  S  L  S  D  R  A  R  L  A  G  A  V  N  T  L  V    91
                                                                        aroE2
401  TGCGTCACGAGGGCCAGTGGCAGGGCGAGAACACCGACGGTATTGGCCTGGTACGTGATCTCACCGATCGTCACGGCCTCGATGATCTGCGCGGTCGCCGT    500
      R  H  E  G  Q  W  Q  G  E  N  T  D  G  I  G  L  V  R  D  L  T  D  R  H  G  L  D  D  L  R  G  R  R  V    124
501  CCTGCTGCTGGGCGCTGCAGGGGCAGCGCGCGGGGTGGCGCCCGTGCCCCTGCTGCAAGCCGGCATTACCGAAATGGTGGTGGTGAACCGCTCGCCGAGCGC    600
      L  L  L  G  A  G  G  A  A  R  G  V  A  P  A  L  L  Q  A  G  I  T  E  M  V  V  V  N  R  S  P  E  R    157
601  GCCGATGCCTTGTGCGGATACATTGGGCGAACCGGGCGTGTCGCGTTACATCGAAGACCTGCGCGACTTCGAGCTGATCGTCAACG    700
      A  D  A  L  C  D  T  L  G  E  P  G  R  V  V  S  R  Y  I  E  D  L  R  D  L  G  D  F  E  L  I  V  N  A    191
                                                                                aroE1
701  CCACCGCGCTGCCGCGACGCGACGCGGGCGCATTCGCGATGCCGCTGGGCGGTGTCAACAGTCTTACCGCGGTCGATCTGAACTATGGCGCCAC    800
      T  A  A  G  R  D  R  D  A  G  A  F  A  M  P  L  G  L  V  N  S  L  T  A  A  V  D  L  N  Y  G  A  T    224
                                                                                HindII
801  TGCCATGCGCTTCCTGGCCGTTCGGCGCTACGCCATGCCCGTTCGGCATGCTGGTAGAGCATGCCGAAAGCTTCGCGGCTG    900
      A  I  A  F  L  A  W  A  R  S  A  Q  C  R  Y  A  I  D  G  L  G  M  L  V  E  H  A  A  E  S  F  A  L    257
901  TGGCATGGCGTGCGCCCAGATACGCCCCAGATACCGCCCAGATACGACCCGGATGACCCGGTGTAGCCGAGGCCGTGCTGGTTCAGTGCCGACTGA    981
      W  H  G  V  R  R  P  D  T  D  P  V  Y  A  A  L  R  A  R  E  A  V  L  V  S  A  D  *    284
```

BACTERIAL MUTANT BX065 AND A METHOD THEREOF

This application claims priority to U.S. Provisional Application 60/279,921 filed Mar. 29, 2001.

FIELD OF THE INVENTION

The present invention relates to a mutant bacteria *Xanthomonas oryzae* pathovar *oryzae* BXO65 with mutation at a site coding for enzyme shikimate dehydrogenase. Also present invention relates to a method of producing said mutant. Further, a method of screening inhibitors of bacterial pathogens with shikimate dehydrogenase pathway to develop bactericides.

BACKGROUND AND PRIOR ART REFERENCES

Every year, plant pathogens cause billions of dollars worth of damage across the globe. Amongst the most destructive classes of plant pathogens are bacteria that grow within the xylem vessels of the host plants. As opposed to fungal pathogens, effective bactericides are not available for protecting plants against bacterial pathogens.

Most of the available compounds are antibiotics (like streptomycin and tetracycline) that are either not effective under field conditions or also affect the host plant. Moreover there is the concern that the use of these antibiotics will result in the spread of antibiotic resistance determinants amongst pathogens that cause disease in humans and other animals. For e.g., tetracycline is one of the drugs of choice for use against *Yersinia pestis* (the plague bacterium). The use of tetracycline against plant pathogens might result in exposure of *Yersinia pestis* to this antibiotic as this bacterium is harbored by rats that populate agricultural fields. There is thus a need for the identification of a new set of targets to develop novel bactericides against plant pathogenic bacteria.

*Xanthomonas oryzae* pathovar *oryzae* (Xoo) is a bacterial pathogen that causes bacterial leaf blight (BLB), a very serious disease of rice. Neither effective bactericides nor resistant rice cultivars are available to reduce yield losses due to this pathogen.

*Xanthomonas oryzae* pv. *Oryzae* causes bacterial leaf blight, a serious disease of rice. Worldwide at least 350 different plant diseases are known to be caused by various xanthomonads (17). A characteristic feature of the genus *Xanthomonas* is the production of yellow, membrane-bound pigments called xanthomonadins (28). The xanthomonadins are initially thought to be carotenoids, but later they are characterized as a unique group of halogenated aryl polyene pigments (2, 3).

The functional role of xanthomonadins is poorly understood. The vast majority of pigment-deficient mutants that have been isolated from several xanthomonads are prototrophs (20, 29) and virulence proficient upon wound inoculation (9, 20, and 29). Pigment-deficient mutants of *Xanthomonas juglandis* and *X. oryzae* pv. *Oryzae* have been reported to be more sensitive to photobiological damage than the wild-type strains are (13, 22), suggesting that the pigment may provide protection against photo-damage.

An 18.6-kb region containing seven transcriptional units required for xanthomonadin biosynthesis has been isolated from *Xanthomonas campestris* pv. *Campestris* (20, 21). One of the transcriptional units, pigB, encodes a diffusible factor that is involved in both pigment and extracellular polysaccharide production (21). The pigB mutants have also been shown to be impaired for epipyhytic survival and host infection (22).

OBJECT OF THE PRESENT INVENTION

The main object of the present invention is to develop bacteria *Xanthomonas oryzae* pathovar *oryzae* BXO65 with mutation at a gene coding for shikimate dehydrogenase.

Another main object of the present invention is to develop a method of producing mutant bacterial strain *Xanthomonas oryzae* pathovar *oryzae* BXO65.

Yet another object of the present invention is to develop a screening method to identify compounds inhibiting shikimate dehydrogenase pathway.

Still another object of the present invention is to identify bactericides against microbes having shikimate dehydrogenase pathway.

Still another object of the present invention is to develop bactericides against bacteria *Xanthomonas oryzae* pathovar *oryzae* causing bacterial leaf blight (BLB) in rice.

SUMMARY OF THE PRESENT INVENTION

The present invention relates to a mutant bacteria *Xanthomonas oryzae* pathovar *oryzae* BXO65 with mutation at a site coding for enzyme shikimate dehydrogenase and a method of producing said mutant and also a method of screening inhibitors of bacterial pathogens with shikimate dehydrogenase pathway to develop bactericides.

BRIEF DESCRIPTION OF THE DRAWINGS

FIG. 3 depicts a nucleotide sequence of *X. oryzae* pv. *oryzae* aroE gene and deduced amino acid sequence. The solid and shaded triangles indicate mTn7 and Tn3-HOHO1 insertions, respectively. The aroE3::mTn7 insertion could not be marked exchanged. The predicted ribosome binding site (S/D) and −35 and −10 promoter regions are indicated. Restriction sites for Eco R1 and Hind III are also indicated.

DETAILED DESCRIPTION OF THE PRESENT INVENTION

In an embodiment, the present invention is a mutant bacteria *Xanthomonas orzae* pv. *orzae* (BXO65).

In another embodiment, the present invention is a mutant bacteria *Xanthomonas orzae* pv. *orzae* (BXO65) wherein said mutant shows mutation in aroE gene coding for shikimate dehydrogenase.

In yet another embodiment, the present invention is a mutant bacteria *Xanthomonas orzae* pv. *orzae* (BXO65) wherein said mutant is avirulent.

In yet another embodiment, the present invention is a mutant bacteria *Xanthomonas orzae* pv. *orzae* (BXO65) wherein doubling time of said mutant is about 25.7 hours.

In still another embodiment, the present invention is a mutant bacteria *Xanthomonas orzae* pv. *orzae* (BXO65) wherein said mutant produces very little Xanthomonadin pigments as compared to wild type.

In still another embodiment, the present invention is a mutant bacteria *Xanthomonas orzae* pv. *orzae* (BXO65) wherein said mutant does not produce aromatic amino acids.

In a further embodiment, the present invention is a method of producing a mutant bacterial strain *Xanthomonas orzae* pv. *orzae* (BXO65).

In still another embodiment, the present invention is a method of producing a mutant bacterial strain *Xanthomonas orzae* pv. *orzae* (BXO65) comprising mutating BXO1 to produce BXO62.

In still another embodiment, the present invention is a method of producing a mutant bacterial strain *Xanthomonas orzae* pv. *orzae* (BXO65) comprising developing rifampin resistance in said BXO62 to produce BXO65.

In still another embodiment, the present invention is a method of producing a mutant bacterial strain *Xanthomonas orzae* pv. *orzae* (BXO65) wherein BXO1 is wild type bacterial strain of *Xanthomonas orzae* pv. *Orzae*.

In still another embodiment, the present invention is a method of producing a mutant bacterial strain *Xanthomonas orzae* pv. *orzae* (BXO65) wherein BXO62 is pigment deficient bacterial strain of *Xanthomonas orzae* pv. *Orzae*.

In still another embodiment, the present invention is a method of producing a mutant bacterial strain *Xanthomonas orzae* pv. *orzae* (BXO65) wherein bacterial strains are grown at 28° C.

In still another embodiment, the present invention is a method of producing a mutant bacterial strain *Xanthomonas orzae* pv. *orzae* (BXO65) wherein said bacterial strains are grown in medium selected from a group comprising peptone sucrose (PS) medium, and modified Miller's minimal medium M4.

In still another embodiment, the present invention is a method of producing a mutant bacterial strain *Xanthomonas orzae* pv. *orzae* (BXO65) wherein mutation is developed by using ethyl methanesulfonate.

In still another embodiment, the present invention is a method of producing a mutant bacterial strain *Xanthomonas orzae* pv. *orzae* (BXO65) wherein rifampin is used at concentration ranging between 25 to 100 µg/ml.

In still another embodiment, the present invention is a method of producing a mutant bacterial strain *Xanthomonas orzae* pv. *orzae* (BXO65) wherein BXO62 strain is obtained at a frequency of 1% of the surviving mutated cells.

In a further embodiment the present invention is a method of producing a mutant bacterial strain *Xanthomonas orzae* pv. *orzae* (BXO65) wherein said method helps develop inhibitors against plant pathogenic bacteria responsible for Bacterial Leaf Blight (BLB) in rice.

In a further embodiment of the present invention is a screening assay system to identify compounds to inhibit Shikimate dehydrogenase pathway in bacteria to develop bactericide.

In still another embodiment the present invention comprises mixing shikimic acid and NADP as substrates.

In still another embodiment the present invention comprises adding test compounds to the said mixture.

In still another embodiment the present invention comprises, measuring change in absorbance at 340 nm.

In still another embodiment the present invention comprises identifying said inhibitors from the test compounds showing decrease in absorbance.

In still another embodiment the present invention comprises identifying said inhibitors from the test compounds showing decrease in absorbance, wherein absorbance is measured spectrophotometrically.

In still another embodiment of the present invention, mixing shikimic acid and NADP shows an increase in absorbance.

In still another embodiment of the present invention, test compounds with inhibitory action show a decrease in absorbance.

In still another embodiment of the present invention, methods of the invention are used to develop inhibitors against pathogenic bacteria having shikimate dehydrogenase pathway.

In still another embodiment of the present invention, test compounds are selected from a group comprising extracts, compounds, biomolecules, and pharmaceutical products.

In a further embodiment the present invention comprises developing aroe gene mutant bacterial plant pathogen *Xanthomonas oryzae* pathovar *oryzae* named BXO65, with mutation in shikimate dehydrogenase and thereby loss of virulence on rice crops.

In an embodiment of the present invention, applicants have determined that Xoo mutants that are defective in the production of the shikimate dehydrogenase enzyme are unable to cause disease on rice.

In another embodiment of the present invention, Shikimate dehydrogenase is a key enzyme in the aromatic amino acid biosynthetic pathway and the virulence deficiency appears to be due to the limited availability of aromatic amino acids within the xylem vessels of the rice plant.

In yet another embodiment of the present invention, shikimate dehydrogenase can be used as a target to develop novel bactericides against Xoo, and possibly against other bacterial pathogens. These bactericides can be in the nature of compounds that affect the shikimate dehydrogenase enzyme of the pathogen without affecting the host.

In still another embodiment of the present invention, the shikimate pathway is a good target for these purposes as it is absent in humans and most animals. Therefore, compounds that target shikimate dehydrogenase may have minimal toxic affects with regard to exposure of humans and other animals to these compounds.

In still another embodiment of the present invention, the judicious application of such compounds could help control yield losses due to Xoo as well as other bacterial pathogens that dwell in the xylem vessels of host plants. Since the shikimate pathway is absent in humans, an additional possibility is that inhibitors of shikimate dehydrogenase may also be used against bacterial pathogens of humans.

In still another embodiment of the present invention, Xanthomonadins are yellow, membrane-bound pigments produced by members of the genus *Xanthomonas*. Applicants identified an ethyl methanesulfonate-induced *Xanthomonas oryzae* pv. *oryzae* mutant (BXO65) that is deficient for xanthomonadin production and virulence on rice, as well as auxotrophic for aromatic amino acids (Pig⁻Vir⁻Aro⁻). Reversion analysis indicated that these multiple phenotypes are due to single mutation.

In still another embodiment of the present invention, a genomic library of the wild-type strain is used to isolate a 7.0-kb clone that complements BX065. By transposon mutagenesis, marker exchange, sequence analysis, and subcloniong, the complementing activity is localized to a 849-bp open reading frame (ORF). This ORF is homologous to the aroE gene, which encodes shikimate dehydrogenase in various bacterial species.

In still another embodiment of the present invention, Shikimate dehydrogenase activity is present in the wild-type strain and the mutant with the complementing clone, whereas no activity is present in BXO65. This clone also complemented an Escherichia Coli aroE mutant for prototrophy, indicating that aroE is functionally conserved in X. oryzae pv, oryzae and E. Coli.

In still another embodiment of the present invention, the nucleotide sequence of the 2.9-kb region containing aroE revealed that a putative DNA helicase gene is located adjacent to aroE. Applicants results indicate that aroE is required for normal levels of virulence and xanthomonadin production in X. oryzae pv. Oryzae.

In still another embodiment of the present invention, the applicants isolated an ethyl methanesulfonate (EMS)-induced pigment-deficient mutant of X. oryzae pv. Oryzae that is also virulence deficient and auxotrophic for aromatic amino acids. A genomic clone that restores pigmentation, prototrophy, and virulence to this mutant is isolated by functional complementation.

In still another embodiment of the present invention, characterization of this clone revealed that shikimate dehydrogenase, an enzyme in the aromatic amino acid biosynthetic pathway, is required for normal levels of pigment production and virulence in X. oryzae pv. Oryzae.

In still another embodiment of the present invention, all bacterial strains and plasmids used are listed in Table 1.

TABLE 1

Strains and Plasmids used in this study

| Strain or plasmid | Relevant Characteristics[a] | Reference or source |
|---|---|---|
| E. coli strains | | |
| DH5α | F' endA1 hsdR17 (r⁻m⁺) supE44 thi-1 recA1 gyrA relA1 f80dlacZDM15 (lacZYA-argF) U169 | Lab collection |
| S17-1 | RP4-2Tc::Mu-Kn::Tn7 pro hsdR recA | 26 |
| AB2835 | AeroE353 | 30 |
| Plasmids | | |
| Pbluescript (KS) | Ap$^r$ | Stratagene, La Jolla, Calif. |
| PHM1 | Sp$^r$ Sm$^r$ cos parA IncW derivative of pRI40 | 11 |
| PUFR034 | IncW Nm$^r$ Tra⁻Mob⁺ mob(P) LacZα⁺ Par⁺ cos | 8 |
| PAG4 | pUFR034 + 7.0-kb EcoRI fragment encoding aroE | This study |
| PAG5 | pBluescript (KS) = 7.0-kb EcoRI fragment encoding aroE | This study |
| PAG7 | Pufr034 + 1.2-kb EcoRI fragment encoding aroE | This study |
| PAG8 | pAG4-aroE1::Tn3-HoHo1 | This study |
| PAG9 | pAG5-aroE2::mTn7 | This study |
| PAG10 | pAG5-aroE3::mTn7 | This study |
| PAG11 | pHM1+ aroE2::mTn7 (in the 7.0-kb EcoRI fragment) | This study |
| PAG12 | pHM1+ aroE3::mTn7 (in the 7.0-kb EcoRI fragment) | This study |
| X. oryzae pv. Oryzae strains | | |
| BXO1 | Laboratory wild type, Indian isolate | Lab collection |
| BXO43 | rif-2, derivative of BXO1 | Lab collection |
| BXO62 | pig-10, obtained by EMS mutagenesis of BXO1 | This study |
| BXO65 | rif-5, derivative of BXO62 | This study |
| BXO1704 | BXO65/pAG4 | This study |
| BXO1706 | aroE1::Tn3-HoHo1 rif-2 | This study |
| BXO1707 | aroE2::mTn7 rif-2 | This study |

[a]rif-2 and rif-5 indicate mutations that confer resistance to rifampin; pig-10 indicates pigment deficiency.

In still another embodiment of the present invention, X. oryzae pv. Oryzae strains are grown at 28° C. in either peptone sucrose (PS) medium or modified Miller's minimal medium M4. Escherichia coli strains are grown in Luria-Bertani medium at 37° C.

In still another embodiment of the present invention, the following concentrations of antibiotics are used: rifampin, 50 μg ml⁻¹; spectinomycin, 50 μg ml⁻¹; ampicillin, 100 μg ml⁻¹; kanamycin 50 μg ml⁻¹; chloramphenicol 20 μg ml⁻¹, streptomycin,50 μg ml⁻¹ and cycloheximide, 75 μg ml⁻¹.

In still another embodiment of the present invention, EMS (Sigma Chemical Co., St. Louis, Mo.) mutagenesis of X. oryzae pv. Oryzae is done as described for E. coli by Miller.

In still another embodiment of the present invention, twenty microliters of a cell suspension from a mutagenized and washed X. oryzae pv. Oryzae cell preparation is inoculated into 2 ml of PS medium and incubated at 28° C. for 24 h before the cells are dilution plated to obtain single colonies of PSagar (PSA) plates.

In still another embodiment of the present invention, pigment-deficient mutants are obtained at a frequency of 1% of the surviving cells. One pigment-deficient mutant failed to grow on minimal medium and the auxotrophic phenotype is diagnosed as a deficiency of all three aromatic amino acids by using the pool plate method.

In still another embodiment of the present invention, spontaneous prototrophic revertants and rifampin-resistant (Rif') derivatives of X. oryzae pv. Oryzae strains are obtained by plating saturated cultures (approximately $10^8$ CFU/plate) on plates containing minimal medium and plates containing PSA plus rifampin, respectively.

In still another embodiment of the present invention, a pigment-deficient mutant (BXY062) that is auxotrophic for all three aromatic amino acids is isolated after EMS mutagenesis of the BXO1 strain.

In still another embodiment of the present invention, to aid in the subsequent analysis, spontaneous Rif' derivatives of BXO1 and BX062 designated BXO43 and BXO65 respectively, are obtained.

In still another embodiment of the present invention, the pigment production, prototrophic-auxotrophic, and virulence properties of the Rif' derivatives are similar to those of their respective parent strains (data not shown). Pigment is extracted from strains BX043 and BX065 and quantified. BX065 produces approximately 23% of the pigment produced by BX043 (Table 2).

TABLE 2

Pigment production and shikimate dehydrogenase activity in various X. oryzae pv. Oryzae strains

| Strain[a] | Pigment production (optical density at 445 nm)[b] | Shikimate dehydrogenase activity (mU/mg of protein)[c] |
|---|---|---|
| BX043 | $0.632 \pm 0.006$[d] | $5.35 \pm 0.57$ |
| BX 065 | $0.15 \pm 0.018$ | NDA[e] |
| BX 01704 | $0.816 \pm 0.03$ | $65.3 \pm 6.07$ |

[a]BX043 is the wild-type strain, BX065 is an EMS-induced Pig⁻ Aro⁻ Vir⁻ mutant, and BXO1704 is BX065 with Pag⁴(a complementing plasmid).
[b]Pigment production was measured by determining absorbance at 445 nm as described in Materials and Methods.
[c]Protein was extracted and shikimate dehydrogenase activity was assayed as described in Materials and Methods.
[d]Mean ± standard error based on three independent experiments.
[e]NDA, no detectable activity.

Figure 1:
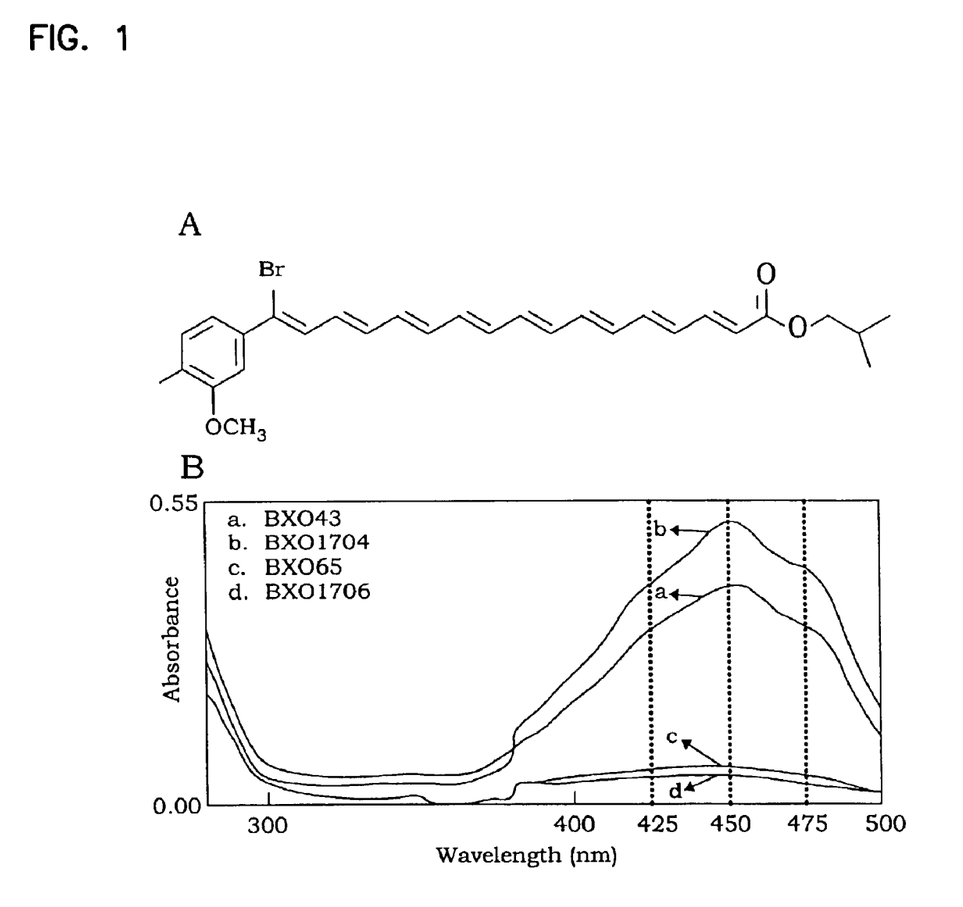
FIG. 1A depicts the structure of isobutyl derivative of xanthomonadin isolated from *X. juglandis*, a walnut pathogen (3).
FIG. 1B depicts absorption spectra of crude pigment extracts from BXO431 (wild-type strain), BXO65 (an EMS-inducted Pig⁻Aro⁻Vir⁻mutant), BXO1706 an aroE1::Tn3-HoHo1 marker exchange mutant), and BXO1704 (BXO65 with a complementing plasmid pAG4). The dashed vertical lines indicate the wavelengths corresponding to the characteristic peak and shoulders in the absorption spectrum of xanthomanadin.

In still another embodiment of the present invention, an absorption spectrum of the pigment extracted from the BX043 strain showed a characteristic structure with peak at 445 nm and shoulders at 425 and 470 nm (FIG. 1). These features are missing from the absorption spectrum of the BX065 strain. (FIG. 1.)

In still another embodiment of the present invention, the virulence characteristics of these strains were assayed with rice leaves as described in Materials and Methods.

Lengths of lesions caused by BXO43 and BXO65 are measured 10 and 15 days after inoculation.

In still another embodiment of the present invention, it is apparent that BXO65 is severely virulence deficient (Vir–). Prototrophic revertants of BXO65 are isolated and are found to have regained pigment and virulence proficiency (data not shown). Simultaneous reversion suggests that a single mutation is responsible for the pleiotropic phenotype of BXO65.

In still another embodiment of the present invention, forty-day-old greenhouse-grown rice plants of susceptible rice cultivar Taichung Native-1 are inoculated by clipping leaf tips with sterile scissors dipped in saturated cultures ($10^8$ cells/ml) of X.oryzae pv. Oryzae.

In still another embodiment of the present invention, when this method is used, approximately $10^8$ cells are deposited at the site of inoculation. The plants are incubated in a greenhouse with minimum and maximum temperatures of approximately 25 and 30° C., respectively, and a relative humidity of approximately 60%.

In still another embodiment of the present invention, lesion lengths are measured at regular intervals. No lesions are observed in control experiments in which the leaves are inoculated with scissors dipped in water.

In still another embodiment of the present invention, the procedure described previous for extraction of xanthomonadin from X. juglandis is used, with some modifications, X. oryzae pv.

In still another embodiment of the present invention, Oryzae cultures are grown to the stationary phase and xanthomonadin is extracted in chloroform-methanol (2:1) by shaking for 3 h at room temperature. The amount of pigment produced per 100 mg. (dry weight) of bacterial cells is expressed as the absorbance (optical density at 445 nm) of the crude pigment extracts.

In still another embodiment of the present invention, applicants also quantified the pigment by assuming that the structure and molar extinction coefficient of xanthomonadin from X. oryzae pv. Oryzae are identical to those of a xanthomonadin from X. juglandis. Similar conclusions could be drawn by using either method for pigment estimation.

In still another embodiment of the present invention, a partial EcoRI-digested genomic library of applicant's laboratory wild-type X.oryze pv. Oryze strain, having an average insert size of 30 kb, is prepared in the broad-host range Km$^r$ cosmid cloning vector pUFR034.

In still another embodiment of the present invention, a total of 960 clones from this library are transferred from E. coli DH5α to S17-1 by using pRK600 as a helper. Genomic clones from the library in S17-1 are mobilized in pools of 12 clones each into the pigment-deficient mutant by performing biparental mating.

In still another embodiment of the present invention, transconjugants that appeared on PSA-rifampin-kanamycin selection plates are replica plated onto minimal medium plates containing kanamycin to identify prototrophic and pigment-proficient colonies.

In still another embodiment of the present invention, clones from a cosmid genomic library of BXO1 are mobilized into BX065 in 55 pools containing 12 clones each.

In still another embodiment of the present invention, we identified three donor pools which yielded Aro⁺ Pig⁺ exconjugants. Individual clones from the three pools are mobilized into BXO65, which led to identification of three independent complementing clones, pAG1, pAG2, and pAG3.

In still another embodiment of the present invention, the EcoRI restriction patterns of the three plasmids revealed that there are three common Eco RI fragments (7.0, 4.0, and 1.5 kb). When the 7.0-kb fragment is subcloned (pAG4) and mobilized into BXO65, it is found to contain the complementing activity.

In still another embodiment of the present invention, the absorption spectrum of the pigment extracted from BXO1704 (BX065/pAG4) is identical to that of BX043 (FIG. 1), and the amount of pigment produced is estimated to be 30% more than the amount produced in the wild type (Table 2).

Figure 2:
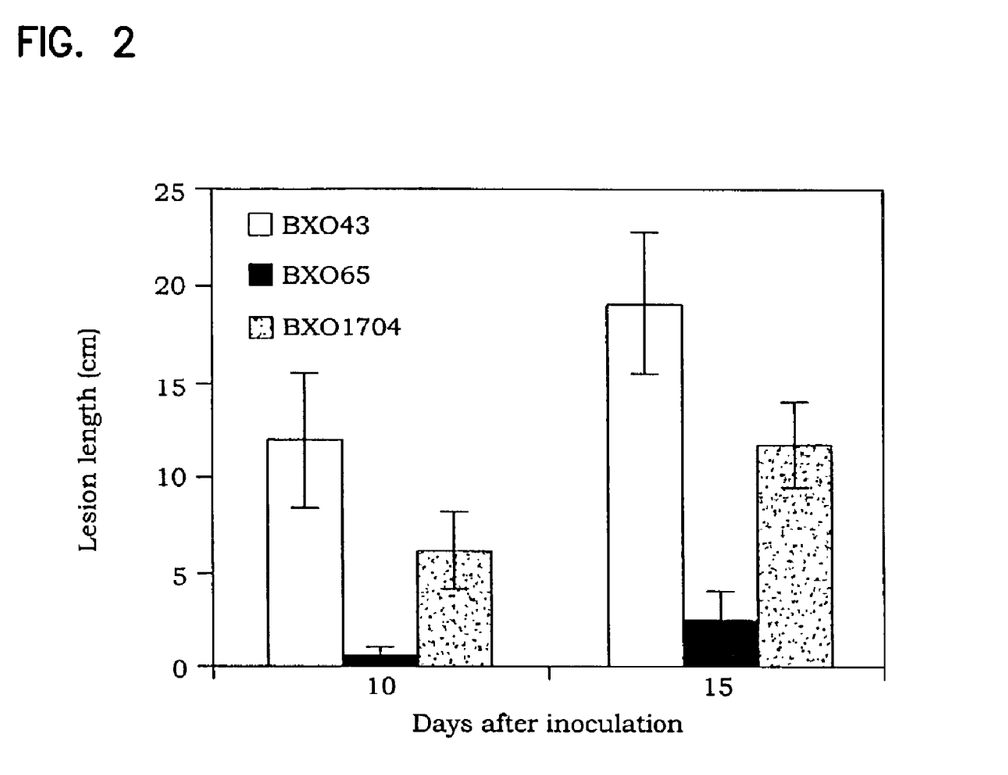
FIG. 2 depicts virulence of *X. oryzae* pv. *oryzae* strains for rice. Inoculations were performed with greenhouse-grown plants of susceptible rice cultivar Taichung Native-1 as described in Materials and Methods. Lesion lengths were measured 10 and 15 days after inoculation. The values are means and standard deviations based on three independent experiments. BXO43, wild-type strain; BXO65, EMS-induced Pig⁻Aro⁻Vir⁻mutant; BXO1704, BXO65 with complementing plasmid pAG4. Similar results were obtained following inoculation of growth chamber-grown rice plants (data not shown).

In still another embodiment of the present invention, this could have been due to the presence of the aroE gene on a multicopy plasmid in BXO1704. The pAG4 plasmid also complemented BX065 partially (~60%) for virulence on rice (FIG. 2). This partial complementation could have been a result of instability of the clone because of the absence of antibiotic selection inside the plant.

In still another embodiment of the present invention, transposon 3 insertions are obtained with the pAG4 clone by using Tn3-HoHo1, with some modifications. Plasmids are isolated, and the insertions are localized on either the insert or the vector DNA by restriction analysis.

In still another embodiment of the present invention, the 7.0-kb EcoRI fragment in pAG4 is also cloned into the EcoRI site of pBluescript(KS) to obtain pAG4 and is mutagenized by mini-transposon 7 (mTn7) derivatives by using an in vitro transposition kit (Genome Priming System; New England Biolabs [NEB], Beverly, Mass.).

In still another embodiment of the present invention, the mTn7 element encodes kanamycin resistance. Two different mTn7 insertions on the cloned DNA in plasmids pAG9 and pAG10 (Table 1) are found to be in the aroE gene (see below). These two insertions are cloned into the shuttle vector pHM1(Sp$^r$) (Table 1) by using EcoRI restriction sites (EcoRI does not cut within the mTn7 element) to obtain plasmids pAG11 and pAG12.

In still another embodiment of the present invention, Plasmids pAG11 and pAG12 and the derivatives of Pag containing Tn3-HoHo1 insertions are mobilized individually into BX0-43 for marker exchange.

In still another embodiment of the present invention, marker exchange is done by growing the cells in either PS-ampicillin medium (for Tn3-HoHo1) or PS-kanamycin medium for (for mTn7) for more than 30 generations by serial passage.

In still another embodiment of the present invention, colonies that are either Ap$^r$ Km$^s$ (for Tn3-HoHo1) or Km$^r$ Sp$^s$ (for mTn7) are analyzed by Southern hybridization to confirm that marker exchange had occurred as expected.

In still another embodiment of the present invention, the 7.0-kb Eco RI fragment in the pAG4 clone is subjected to mutagenesis by using Tn3-HoHo1 and mTn7.

In still another embodiment of the present invention, seven independent Tn3-HoHo1 insertions are obtained on pAG4, and one of them, aroE1::Tn3-HoHo1, affected the ability to complement BX065 (data not shown). This insertion is marker exchanged in the BX043 background. The marker exchange mutant BXO1706 is found to be Pig$^-$(FIG. 1), Vir$^-$(data not shown), and auxotrophic for aromatic amino acids.

In still another embodiment of the present invention, introductions of pAG4 into BXO1706 restored the Pig$^+$ Vir$^+$ Aro$^+$ phenotype (data not shown). This indicated that aroE1::Tn3-HoHo1 disrupted a transcriptional unit that is required for pigmentation, virulence, and prototrophy.

In still another embodiment of the present invention, Marker exchange mutants obtained with six other Tn3-HoHo1 insertions are Pig$^+$ Vir$^+$ Aro$^+$. Twenty-nine mTn7 insertions are obtained for the 7.0-kb DNA cloned in pAG5 (see Materials and Methods). Two of these insertions, aroE2::mTn7 AND aroE3::mTn7 in plasmids pAG9 and pAG10, respectively, are found to be in the aroE open reading frame (ORF). These two insertions along with flanking 7.0-kb sequences are cloned in the EcoRI site of the plasmid shuttle vector pHM11 to give plasmids pAGI 1 and pAG12.

In still another embodiment of the present invention, both pAG11 and pAG12 failed to complement BX065, indicating that aroE2::mTn7 and aroE3::mTn7 abolished the complementing ability of the 7.0 kb genomic fragment. When the aroE2::mTn7 insertion is marker exchanged in the BX043 background, it produced the Pig$^-$ Vir$^-$ Aro$^-$ mutant strain BXO1707 (data not shown). The aroE3::mTn7 insertion could not be marker exchanged, most likely because of limited homology on one side of the insertion (FIG. 3).

In still another embodiment of the present invention, plasmid DNA is isolated by the alkaline lysis method.

In still another embodiment of the present invention, Restriction digestions are performed by using enzymes obtained from NEB as recommended by the supplier. Primers that are outwardly directed from Tn3-HoHo1 are used to obtain the sequence of DNA flanking the Tn3-HoHo1 insertions. mTn7-specific primers provided in the Genome Priming System kit from NEB are used to sequence the mTn7 insertion sites. M13 forward and reverse primers are used to sequence to ends of a 7.0-kb insert in clone pAG5.

In still another embodiment of the present invention, the sequencing reactions, electrophoresis, and sequence data analyses are performed with an ABI Prism 377 automated DNA sequencer (Perkin-Elmer, Foster City, Calif.).

In still another embodiment of the present invention, a homology search in the database is performed through the National Center for Biotechnology Information by using the BLAST algorithm (1). Promoter prediction is performed by using software at the Baylor College of Medicine search launcher.

In still another embodiment of the present invention, the sequence of a 2.953-kb region containing aroE is determined. This sequence has been submitted to GenBank with accession no. AF258797.

In still another embodiment of the present invention, a 2.953-kb region cloned in pAG5 is sequenced by using transposon-specific primers, as well as primer walking.

In still another embodiment of the present invention, the insertions aroE1::Tn3-HoHo1, aroE2::mTn7, and aroE3::mTn7 are found to be present in a 849-bp ORF with the potential to encode a 283-amino-acid protein (FIG. 3).

In still another embodiment of the present invention, a homology search using the BLAST algorithm revealed that the ORF is homologous to aroE, which encodes shikimate dehydrogenase, an enzyme in the aromatic amino acid biosynthetic pathway of various bacterial species.

In still another embodiment of the present invention, maximum homologies are found with aroE from Pseudomonas aeruginosa (EMBL/GenBank/DDBJ database accession no. X85015), Neisseria meningitidis, E. coli, and Haemophilus influenzae, as shown in Table 3.

TABLE 3

Homology of the X. oryzae pv. Oryzae aroE gene with the aroE genes of other bacterial species

| Organism | Length of gene product (amino acids) | % similarity (% identity) | E value | Accession no |
|---|---|---|---|---|
| *P. aeruginosa* | 274 | 58(45) | e-54 | X85015 |
| *N. meningitidis* | 269 | 57(41) | e-50 | U82840 |
| *E. Coli* | 272 | 58(44) | e-50 | U18997 |
| *H. influenzae* | 272 | 53(38) | e-35 | U32748 |

E values were obtained by using the Blast algorithm.

In still another embodiment of the present invention, promoter prediction, as described in Materials and Methods, indicated the presence of −35 and −10 promoter regions 100 and 75 nucleotides upstream of the putative ATG start codon, respectively.

In still another embodiment of the present invention, within the ORF the aroE1::mTn3-HoHo1, aroE2::mTn7, and aroE3::mTn7 insertions are located at the $634^{th}$, $350^{th}$, and $15^{th}$ nucleotides, respectively (FIG. 3). A PstI restriction site is identified 200 bp downstream of the aroE stop condon. This site is used to clone a 1.2-kb EcoRI-PstI fragment that included the aroE ORF to obtain plasmid pAG7. When pAG7 is introduced into BX065, this minimal fragment is sufficient to confer the Pig+ Vir+ Aro+ phenotype (data not shown).

In still another embodiment of the present invention, in the 2.953-kb sequence, another ORF downstream of aroE is identified by using the BLAST algorithm. This incomplete ORF started at $1,546^{th}$ nucleotide and showed very strong homology in the 1,407 bp sequenced (55% similarity and 36% identity at the amino acid level) to dinG (DNA damage-inducible gene G), which encloides an ATP-dependent helicase in E.coli.

In still another embodiment of the present invention, E. coli aroE mutant strain AB2835 (30) is transformed individually with pAG4 and pAG5 and with plasmids pAG8, pAG9, and pAG10 having transposon insertions in the aeroE ORF (Table 1).

In still another embodiment of the present invention, Plasmids pAG4 and pAG5 complemented AB2835 for growth on minimal medium, whereas the other plasmids having an insertion in the aroE ORF are not able to do so.

In still another embodiment of the present invention, all strains grew on minimal medium supplemented with the three aromatic amino acids and the aromatic vitamins p-aminobenzoic acid and p-hydroxybenzoic acid. Plasmid curing from strain AB2835/pAG4 resulted in a loss of prototrophy (data not shown).

In still another embodiment of the present invention, cell lysates are prepared as described by Chaudhuri and Coggins, and protein contents are estimated by the Bradford method (5). Shikimate dehydrogenase activities in cell lysates of X. oryzae pv. Oryzae strains are assayed as described previously for E. coli.

In still another embodiment of the present invention, Shikimic acid and NDAP are used as substrates, and reduction of NADP to NADPH is assayed by monitoring increase in absorbance at 340 nm. One unit of enzyme activity is defined as 1 $\mu$mol of NADPH produced per min.

In still another embodiment of the present invention, protein extracts are prepared from the wild-type and aroE mutant strains of *X. oryzae* pv. *Oryzae,* and shikimate dehydrogenase activity is measured (see Materials and Methods).

In still another embodiment of the present invention, the Michaelis constant of this enzyme for shikimic acid is calculated to be $5\times10^{-5}$M, a value very similar to that *E. coli* (32). The enzyme activity is found to be 5.4 mU/mg of protein in wild-type strain BX043 (Table 2).

In still another embodiment of the present invention, no activity is detected in aroE mutant-strain BX065 or in BX01706(aroE1::Tn3-HoHo1) or BXO1707 (aroE2::mTn7). The BXO1704 strain (BX065/pAG4) had an activity of 65 mU/mg of protein, approximately 12 times that of BX043 (Table 2).

In still another embodiment of the present invention, cross-feeding of BX065 with 15 independently isolated EMS-induced prototrophic pigment-deficient mutants is tested by streaking the mutant strains adjacent to BX065 in pairwise combinations on PSA plates.

In still another embodiment of the present invention, development of a yellow color in BXO65 at the adjacent colony boundary is considered to indicate cross-feeding for pigmentation.

In still another embodiment of the present invention, BXO65 could not be cross-fed for pigmentation by wild-type strain BX043, whereas 8 of 15 EMS-induced prototrophic pigment-deficient mutants could do so.

In still another embodiment of the present invention, none of the 15 prototrophic pigment-deficient mutants could be cross-fed by each other BX043, or BX065 for pigmentation.

In still another embodiment of the present invention, mutations in the aroE gene of *X. oryzae* pv. *Oryzae* result in reduced levels of xanthomonadin production and virulence. To the best of our knowledge, this is the first report of a mutation affecting a specific step in a general metabolic pathway that also affects xanthomonadin biosynthesis.

In still another embodiment of the present invention, insertional inactivation of any of the seven transcriptional units previously shown to be required for xanthomonadin biosynthesis in *x. campestris* pv. *Campestris* has not been reported to cause any nutrient deficiences.

In still another embodiment of the present invention, also, clones containing the aroE gene of *X. oryzae* pv. *Oryzae* do not show any homology with the pig gene cluster of either *X. campestris* pv. *Campestris* or *X. oryzae* pv. *Oryzae.* This indicates that the aroE gene is from a different genomic locus than the gene cluster that was previously shown to be required for xanthomonadin biosynthesis.

In still another embodiment of the present invention, shikimate dehydrogenase catalyzes the conversion of dehydroshikimate to shikimic acid. How might shikimate production be related to xanthomonadin biosynthesis? One possibility, as previously suggested, is that the aromatic ring in xanthomonadin may be derived from the shikimate pathway. This would be interesting because the aromatic ring in aromatic carotenold pigments is derived from cyclization of the polyene chain and not from the shikimate pathway. However, we have observed that shikimic acid facilitates neither growth on minimal medium nor pigmentation in aroE mutants (Goel and sonti, unpublished results). This might be because aroE mutants of *X. oryzae* pv. *Oryzae* are deficient in shikimic acid uptake, as reported previously for *E. coil* aroE mutants.

In still another embodiment of the present invention, the residual amount of pigment made in the aroE mutants may be derived either from a very small amount of shikimic acid produced by spontaneous conversion of dehydroshikimate to shikimic acid or through a second minor pathway. It is also possible that the pigment produced by the aroE mutants is devoid of the aromatic ring.

In still another embodiment of the present invention, detailed structural analysis and biochemical experiments, such as feeding wild-type cells with labelled shikimic acid and monitoring the incorporation of the label, are required to address these issues.

In still another embodiment of the present invention, several EMS-induced pigment-deficient mutants are able to cross-feed aroE mutant strains for pigment production. This suggests that a diffusible compound that can enter the pigment biosynthetic pathway accumulates in these stains.

In still another embodiment of the present invention, as xanthomonadins are membrane-bound pigments, the compound or intermediate must act prior to commitment to the membrane-bound state.

In still another embodiment of the present invention, the inability of the wild-type strain and some of the EMS-induced mutants to cross-feed aroE strains suggests that the compound does not accumulate in these strains.

In still another embodiment of the present invention, the inability of the prototrophic EMS-induced pigment-deficient mutants to cross-feed each other suggests that they are defective in reactions that involve commitment to either the membrane-bound state or subsequent steps in xanthomonadin production and transport.

In still another embodiment of the present invention, the virulence deficiency of the aeroE mutants is most likely due to a growth defect. The in planta doubling times for the wild type, aroE mutant BXO65, and a mutant with a complementing clone are 8.6, 25.7, and 10.5 h, respectively (data not shown).

In still another embodiment of the present invention, this is the first report which suggests that one or more aromatic amino acids may be limiting for growth of *X. oryzae* pv. *oryzae* in rice plants. A virulence deficiency has previously been reported to be associated with either arginine or leucine auxotrophy in *X. oryzae* pv. *oryzae*.

In still another embodiment of the present invention, the results also suggest that shikimate dehydrogenase can be used as a target to develop novel bactericides against *X. oryzae* pv. *oryzae*. These bactericides can be compounds that affect the shikimate dehydrogenase of the pathogen without affecting the host. The shikimate pathway may be a good target for this purpose as it is absent in mammals.

In still another embodiment of the present invention, it is pertinent to note that effective bactericides are not available for use against *X. oryzae* pv. *oryzae* and that judicious application of such compounds could help control yield losses due to this devastating rice pathogen.

The details of the present invention are illustrated below with the help of examples but should not be construed to limit the scope of the invention.

EXAMPLES

Example 1
Overexpression and Purification of Shikimate Dehydrogenase Enzyme of *Xanthomonas oryzae* pathovar *oryzae*.

The plasmids pAG7 containing aroE and the pGEX2T (Pharmacia Biotech, Upsaala, Sweden) are purified from cultures of *Escherichia coli* by the alkaline lysis method (25). PCR (Polymerase Chain Reaction) primers for the aroE gene are designed, by methods familiar to those well versed in the art, to incorporate the sites for BamHl and EcoRL. PCR is performed with Vent Polymerase (NEB) using pAG7 DNA as template to obtain a single fragment of approximately 870 bp. This fragment is digested with restriction enzymes BamH1 and EcoRI obtained from NEB. This fragment is cloned into the BamHI and EcoRI sites of pGEX2T using standard procedures as described (25) to generate a fusion of the shikimate dehydrogenase (aroE) alongwith the gene for glutathione-S-transferase that is encoded on pGEX2. Exponentially growing *E. coli* cultures containing this recombinant aroE plasmid are induced with IPTG (Isopropyl thio galactoside; a potent inducer of the promoter to which aroE gene is fused) to produce large amounts of the shikimate dehydrogenase fusion protein. The uninduced plasmid does not produce the fusion protein. The cells are lysed and the overexpressed shikimate dehydrogenase-glutathione S-transferase fusion protein is purified using glutathione agarose beads as per manufacturer's (Pharmacia) instructions. Shikimate dehydrogenase protein is obtained by cleaving the fusion protein with thrombin as per manufacturer's (Pharmacia) instructions.

Example 2
Development of a Screening Procedure for Identifying Inhibitors of Shikimate Dehydrogenase Enzyme of *Xanthomonas oryzae* Pathovar *oryzae*.

The purified shikimate dehydrogenase enzyme can be used in enzyme assays (32) to identify chemicals that are inhibitory to the activity of the enzyme. The assay involves use of Shikimic acid and NADP as substrates. The reduction of NADP to NADPH is followed by monitoring increase in absorbance at 340 nm. The inhibitors would be chemicals that would prevent/reduce enzyme mediated conversion of NADP to NADPH as monitored by following absorbance at 340 nm. The total reaction volume would be $100\mu$ liters, sufficient to be accommodated in the $250\mu$ liter wells of ELISA plates. The absorbance can be followed on an ELISA spectrophotometer. The reaction is rapid and proceeds to saturation in thirty seconds to one mimjte. This facilitates the screening of a large number of candidate inhibitor molecules. The procedure can be automated, wherein liquid handling systems can be used for pipetting various reaction ingredients including enzyme, substrates, buffer, inhibitors, etc. The procedure for spectrophotometric analysis can also be automated, facilitating the screening of a large number of chemical libraries. These procedures for automation are routinely used in drug discovery programmes all over the world and can be adapted to screen for shikimate dehydrogenase inhibitors using the above assay with the purified enzyme.

Example 3
Development of a Screening Procedure for Identifying Inhibitors of Shikimate Dehydrogenase Enzyme of *Xanthomonas oryzae* Pathovar *oryzae* Using the Cloned *X. oryzae* Pathovar *oryzae* aroE Gene (PAGS).

The principle of this method is that a strain carrying shikimate dehydrogenase gene on a high copy number plasmid (pAG5; pBluescript is the vector) will produce higher amounts of shikimate dehydrogenase and can therefore tolerate higher concentrations of shikimate dehydrogenase irihibitor. The host strain would be an *E. coli* wild type strain containing either pAG5 (table 1) or the pBluescript vector without added insert. The use of *E. coli* is doubly advantageous because it grows faster than *X. oryzae* pv. *oryzae* and the high copy number plasmid (copy number of 500–1000/cell) can replicate in *E. coli* and not in *X. oryzae* pv. *oryzae*. Results presented demonstrate that the *X. oryzae* pv. *oryzae* gene is expressed and will functionally complement an *E. coli* aroE mutant. The criteria for a shikimate dehydrogenase enzyme inhibitor would be retardation of growth on minimal medium of an *E. coli* strain that carries the high copy number plasmid (without aroE gene) with either little or no effect on a strain that has the aroE gene on a high copy plasmid. The growth assays can be performed in 96 well ELISA plates and growth can be followed by change in absorbance at 600 nm in ELISA spectrophotometer. Again, this is a procedure that can be automated.

Example 4
Assay for Inhibition of Growth of *Xanthomonas oryzae* Pathovar *Oryzae* by Inhibitors of Shikimate Dehydrogenase.

The inhibitors of shikimate dehydrogenase identified by assays conducted as described in Examples 2 and 3 are screened for their ability to inhibit growth of *Xanthomonas oryzae* pathovar *oryzae* onjninimal mediumprepared as described (15). Saturated cultures of the wild type *X. oryzae* pathovar *oryzae* grown in minimal medium are diluted ten fold in double distilled water and plated onto minimal medium agar plates containing different concentrations of the inhibitor in the presence or absence of aromatic amino acids. An inhibitor of shikimate dehydrogenase should prevent growth of *X. oryzae* pathovar *oryzae* only on minimal medium that is not supplemented with aromatic amino acids. This inhibitor should also inhibit xanthomonadin production which can be assayed as lack (or reduced amounts) of the characteristic yellow pigmentation. The assay for reduction in xanthomonadin production is performed on Peptone Sucrose Agar (29) medium.

Example 5
Assay for Effects on Rice Plants of Identified Inhibitors of *X. oryzae* Pathovar *Oryzae* Shikimate Dehydrogenase.

Forty to fifty day old green house grown rice plants of cultivars Taichung Native-1 and BPT5204 (a fine quality rice from South India) are sprayed with solutions of different concentrations of the inhibitor and compared with those that are sprayed only with the solvent (water). The plants are subjected to a second round of spraying, 36 hours after the initial spaying. The plants are examined at regular intervals, prior to and after the second round of spraying, for symptoms of chlorosis (loss of green coloration), stunting (growth inhibition) and at later stages for defects in the emergence of panicle (rice inflorescence). *X. oryzae* pathovar oryzae is also a seed borne pathogen and therefore bactericides would also be used to used to rid the seeds of infestation by this pathogen. Therefore any potential bactericide would have to be examined to determine if it has adverse effects on seed germination. For this purpose, rice seeds would be germinated in growth chambers or incubators, at 28° Centigrade, on moistened filter paper containing different concentrations of the inhibitor. Germination is assayed after 72–96 hours as emergence of radicals (roots) and shoots. Shikimate dehydrogenase assays can also be performed as described in Example 2, on crude protein extracts of rice leaves, in order to determine if any of the tested compounds will affect rice shikimate dehydrogenase activity.

Example 6
Assay for Amelioration of Bacterial Leaf Blight Symptoms of Rice by Identified Inhibitors.

Forty to fifty day old green house grown rice plants of cultivars Taichung Native-1 and BPT5204 (a fine quality rice from South India) are inoculated with saturated cultures of *X. oryzae* pathovar *oryzae* by either clipping (14) or dipping leaves in bacterial culture. In the latter method of infection, which is more akin to natural conditions, the bacterium must enter the plant through natural openings called hydathodes. Twelve hours after inoculation an optimum concentration of the inhibitor (identified in Examples 4 and 5) that would not inhibit growth of rice but would inhibit *X. oryzae* pathovar *oryzae* is sprayed over these plants. Control plants would also be sprayed with water alone (no inhibitor). Small amounts of a surfactant such as Tween 20 will also be added to test solutions as well as the control in order to facilitate absorption by the leaf. This procedure is repeated 36 hours later. After an additional week on the greenhouse bench, the leaves are examined for bacterial leaf blight symptoms. The efficiency of infection (number of leaves exhibiting symptoms of bacterial leaf blight/total number of infected leaves) as well as the length of the lesions are estimated. An effective inhibitor would be one that reduces efficiency of infection as well as lesion length.

Example 7
A Procedure for Identification of Inhibitors that Affect Shikimate Dehydrogenase of *X. oryzae* Pathovar *Oryzae* but not Shikimate Dehydrogenase of Rice.

An alternative procedure for identification of inhibitors that affect shikimate dehydrogenase of *X. oryzae* pathovar *oryzae* but not shikimate dehydrogenase of rice can be followed when the sequence of rice shikimate dehydrogenase becomes available after completion of the rice genome sequence in the next year or two. The deduced amino acid sequences of the two shikimate dehydrogenase can be used to model the structures of these enzymes using computer assisted procedures (35). Based on these structures, molecular modeling methods which are familiar to those well versed in the art of drug discovery, can then be used to identify inhibitors/lead molecules that might inhibit shikimate dehydrogenase of *X. oryzae* pathovar *oryzae* and not affect shikimate dehydrogenase of rice.

FIG. 1 shows structure of Xanthomonadin I and absorption spectra of crude pigment extracts from *X. oryzae* pv. *oryzae* cultures. (A) Structure of isobutyl derivative of xanthomonadin isolated from *X. juglandis,* a walnut pathogen. (B). Absorption spectra of crude pigment extracts from BXO43 1 (wild-type strain), BXO65 (an EMS-induced pig$^-$ Aro$^-$ Vir$^-$ mutant), BXO1706 an aroE1::Tn3-HoHo1 marker exchange mutant), BXO1704 (BX065 with a complementing plasmid pAG4). The dashed vertical lines indicate the wavelengths corresponding to the characteristic peak and shoulders in the absorption spectrum of xanthomanadin.

FIG. 2 shows Virulence of *X. oryzae* pv. *Oryzae* strains for rice. Inoculations are performed with greenhouse-grown plants of susceptible rice cultivar Taichung native-1. Lesion lengths are measured 10 and 15 days after inoculation. The values are means and standard deviations based on three independent experiments. BXO43, wild-type strain; BXO65, EMS-induced Pig$^-$ Aro$^-$ Vir$^-$ mutant; BXO1704, BXO65 with complementing plasmid pAG4. Similar results are obtained following inoculation of growth chamber-grown rice plants.

FIG. 3 shows nucleotide sequence of *X. oryzae* pv. *Oryzae* aroE gene and deduced amino acid sequence. The solid and shaded triangles indicate mTn7 and Tn3-HOHO1 insertions, respectively. The aroE3::mTn7 insertion could not be marker exchanged. The predicted ribosome binding site (S/D) and −35 and −10 promoter regions are indicated. Restriction sites for EcoRI and HindIII are also indicated.

REFERENCES

1. Altschul, S. F., T. L. Madden. A. A. Schaffer, J. Zhang, W. Mifler and D. J. Lipman, 1997. Gapped BLAST and PSI-BLAST; a new generation of protein database search programs. Nucleic Acids Res. 25:3389–3402.
2. Andrews, A. G., Hertzberg, S. L. Jensen, and M. P. Starr. 1973. Xanthomonas pigments. 2. The *Xanthomonas* "Caratenoids"—non-caratenoids brominated aryl-polyene esters. Acta Chem. Scand. 27:2383–2395.
3. Andrewes, A. G., C. L. Jenkins, M. P. Star, J. Sheperd, and H. Hope.1976. Structure of xanthomonadin I, a novel dibrominated aryl-polyene pigment produced by the bacterium *Xanthomonas juglandis*. Tetrahendron Lett 45:4023–4024.
4. Anton, I. A., and J. R. Coggins. 1988. Sequencing and Overexpression of the *Escherichia coli* aroE gene encoding shikimate dehydrogenase. Biochem. J. 249:319–326.
5. Bradford, M. M. 1976. A rapid and sensitive method for quantitation of microgram quantities of protein utilizing the principle of protein-dye binding. Anal. Biochem. 72:248–254.

6. Chaudhuri, S. and J. R. Coggins. 1985. The purification of shikimate dehydrogenase from *Escherichia coli*. Biochem. J. 226:217–223.
7. Davis, R. W., D. Botstein, and J. R. Roth. 1980. A manual for genetic engineering: advanced bacterial genetics. Cold Spring Harbor Laboratory Press, Cold Spring Harbor, N.Y.
8. DeFeyter, R., C. I. Kado, and D. W. gabriel. 1990. Small stable shuttle vectors for use in *Xanthomonas*. Gene 88:65–72.
9. Durgapal, J. C. 1996. Albino mutation in rice bacterial blight pathogen. Curr, Sci. 70:15.
10. Fleischman, R. D., M. D. Adams, O. White , R. A. Clayton, E. F. Kirkness, A. R. Keriavage, C. J. Bult, J. F. Tomb, B. A. Dougherty, J. M. Merrick, K. McKenney, G. Sutton, W. Fitzhugh, C. A. fields, J. D. Gocayne, J. D. Scott, R. Shirley, L. I. Liu, a. Glodek, J. M. Kelley, J. F. Weidman, C. A. Phillips, T. Spriggs, E. Hedblom, M. D. Cotton, T. R. Utterback, M. C. Hanna, D. T. Nguyen, D. M. Saudek, R. C. Brandon, L. D. Fine, J. L. Fritchman, J. L. Fuchrmann, N. S. M. Geoghagen, C. L. Gnehm, L. A. McDonald, K. V. Small, C. M. Fraser, H. O. Smith, and J. C. Venter. 1995. Whole genome random sequencing and assembly of *Haemophilus influenza* Rd. Science 269:496–512.
11. Innes, R., M. Hirose, and P. Kuempel. 1988. Induction of nitrogen fixing nodules on clover requires only 32 kilobase pairs of DNA from the *Rhizohium trifolii* symbiosis plasmid. J. Bacteriol. 170:3793–3802.
12. Jenkins, C. L., and M. P. Starr. 1982. The pigment to xanthomonadin pigment group II. Curr. Micronbiol. 7:195–198.
13. Jekins, C. L., and M. P. Starr. 1982. The brominated aryl polyene (xanthomonadin) pigments of *X. juglandis* protect against aphotobiologi8cal damage. Curr. Microbiol. 7:323–326.
14. Kauffmann, H. E., A. P. K. Reddy, S. P. Y. Hsieh, and S. D. Mrca. 1973. An improved technique for evaluation of resistence of rioce varieties to *Xanthomonas oryzae*. Plant Dis. rep. 57:537–541.
15. Keremu, S., and J. K. Leach. 1990. Cloning and characterization of an avirulence gene from *Xanthomonas campestris* pv. *oryzae*. Mol. Plant-Microbe Interact. 3:59–65.
16. Lewis, L. K., and D. W. Mount. 1992, Interaction of LexA repressor with the assymmetric dinG operator and complete nucleotide sequence of the gene. J. Bacterio. 174:5110–5116.
17. Leyns, F., M. DeCleene, J. G. Swings, and J. Deley. 1984. The host range of the genus *Xanthomonas*. Bot. Rev. 50:308–356.
18. Miller, J. H. 1992. A short course in bacterial genetics: a laboratory manual for *Escherichia coli* and related bacteria. Cold Spring Harbor laboratory Press, Cold Spring Harbor, N.Y.
19. Pittard, J., and B. J. Wallace. 1966. Distribution and function of genes concerned with aromatic biosynthesis in *Escherichia* in *Escherichia coli*. J. bacteriol. 91:1494–1508.
20. Poplawsky, A. R., M. D. Kawalek, and N. W. Schadd. 1993. A xanthomonadin-encoding gene cluster for the identification of pathovars of *Xanthomonas Campestris*. Mol. Plant-Microbe Interact. 6:545–552.
21. Poplawsky, A. R., and W. Chun. 1998. *Xanthomonas campesits* py. *Campestris*. J. Bacteriol. 179:439–444.
22. Poplawsky, A. R., and W. Chun. 1998. *Xanthomonas campestris* pv. *Campestris* requires a functional pigB for epiphytic survival and host infection. Mol. Plant-Microbe Interact. 11:466–475.
23. Rajagopal, L., C. Sivakamasundari, D. Balasubramanian, and R. V. Sonti. 1997. The bacterial p pigment xanthomonadin provides protection against photodamage. FEBS Lett. 415:125–128.
24. Rajagopal, L., S. Dharmapuri, A. T. Sayeepriyadarshini, and R. V. Sonti. 1999. A genomic library of *Xanthomonas oryzae* pv. *Oryzae* in the broad host range mobilizing *Escherichia coli* strain S17-1. Int. Rice Res. Notes 24:20–21.
25. Sambrook, J., E. F. Fritsch, and T. Maniatis. 1989. Molecular cloning: a laboratory manual, $2^{nd}$ ed. Cold Spring Harbor Laboratory Press, Cold Spring Harbor, N.Y.
26. Simon, R., U. Preifer, and A. Puhler. 1983. A broad host range mobilisation system for in vivo genetic engineering: transposon mutagenesis in gram negative bacteria. Bio/Technology 1:784–791.
27. Stachel, S. E., G. An, C. Flores, and E. W. Nester. 1985. A TnZ lacZ transposon for random β-galactosidase gene fusions: application to the analysis of gene expression in *Agrobacterium*. EMBO J. 4:891–898.
28. Starr, M. P. 1981. The genus *Xanthomonas*, p. 742–763. In M. P. Starr, H. vol. 1. Springer-Verlag, Berlin, Germany.
29. Tsuchiya, K., T. W. Mew, and S. Wakimoto. 1982. Bacteriological and pathological characteristics of wild type and induced mutants of *Xanthomonas campestris* pv. *oryzae*. Phytopathology 72:43–46.
30. Whipp, M. J., H. Camakaris, and A. J. Pittard. 1998. Cloning and analysis of shiA Gene, which encodes the shikimate transport system of *Escherichia coli* K-12. Gene 209:185–192.
31. Yamasaki, Y., N. Murata, and T. Suwa. 1964. The effect of mutations for nutritional requirements on the pathogenicity of two pathogens of rice. Proc. Jpn. Acad. 40:226–231.
32. Yaniv, H., and C. Gilvarg, 1955. Aromatic biosynthesis. XIV. 5-Dehydroshikimic reductases. J. Biol. Chem. 213:787–795.
33. Zbou, J., L. D. Bowler, and B. G. Spratt. 1997. Interspecies recombination and phylogenetic distortions within the glutamine synthetase and shikimate dehydrogenetic genes of *Neisseria meningitidis* and commensal *Neisseria* species. Mol. Mocrobiol. 23:799–812.
34. Poplawsky, A. R., S. C. Urban, and W. Chun. 2000. Biological role of xanthomonadin pigments in *Xanthomonas campestris* pv. *campestris*. Appl. Environ. Microbiol. 66: 5123–5127.
35. Baker, D., and A. Sali. 2001. Protein structure prediction and structural genomics. Science. 294: 93–96.

What is claimed is:

1. An isolated mutant bacteria *Xanthomonas oryzae* pv. *oryzae,* wherein said mutant comprises a mutation in aroE gene coding for shikimate dehydrogenase.

2. An isolated mutant as claimed in claim 1, wherein said mutant is avirulent.

3. An isolated mutant as claimed in claim 1, wherein doubling time of said mutant is about 25.7 hours.

4. An isolated mutant as claimed in claim 1, wherein said mutant produces less *Xanthomonadin* pigments as compared to wild type.

5. An isolated mutant as claimed in claim 1, wherein said mutant does not produce aromatic amino acids.

6. An isolated mutant bacteria *Xanthomonas oryzae* pv. *oryzae* BXO65 having MTCC accession number 5156.

* * * * *

SEQUENCE LISTING

<160> NUMBER OF SEQ ID NOS: 2

<210> SEQ ID NO 1
<211> LENGTH: 981
<212> TYPE: DNA
<213> ORGANISM: Xanthomonas oryzae

<400> SEQUENCE: 1

```
gaattcagca agccccgaag cagacgggac gcagagtaga cttgccgcca gcgtgagcag 60
cgccatcgat agtgcatgcg gtgttcctgc ctcaagtcgc gcacagtcta gtcaaccaga 120
gagcgtttca tgcccgtatc ccgttatgcc gtgttcggtc accccgtcgc ccattccctg 180
tcgccggcta tccatgccga cttcgggaag cagaccggca ttgtgctgga ctacaccgcc 240
atcgatgcgc cgccggagga cttcagtgcc gcgctgcaac gcttcgccga tggaggcggc 300
aagggtgcga acgtcaccct gccgttgaaa gaagcggcct gtgcgctggc cagtagcctc 360
agcgatcgcg cgcggctggc cggggcggtg aacaccctgg tgcgtcacga gggccagtgg 420
cagggcgaga acaccgacgg tattggcctg gtacgtgatc tcaccgatcg tcatggcctg 480
gatctgcgcg gtcgccgcgt cctgctgctg ggcgccggcg gcgctgcacg cggcgtggcg 540
ccggcactgc tgcaagccgg cattaccgaa atggtggtgg tgaaccgctc gcccgagcgc 600
gccgatgcgt tgtgcgatac attgggcgaa cccgggcgcg tggtgtcgcg ttacatcgaa 660
gacctgcgcg atctgggcga cttcgagctg atcgtcaacg ccaccgccgc tggccgcgac 720
cgcgacgctg ggcattcgc gatgccgctg ggctggtca acagtcttac cgctgcggtc 780
gatctgaact atggcgccac tgccatcgcg ttcctggcgt gggcgcgttc ggcgcaatgc 840
cggtacgcca tcgacggctt gggcatgctg gtagagcatg ccgccgaaag cttcgcgctg 900
tggcatggcg tgcgcccaga taccgacccg gtctacgccg cgctgcgcgc gcgcgaggcc 960
gtgctggtca gtgccgactg a 981

<210> SEQ ID NO 2
<211> LENGTH: 283
<212> TYPE: PRT
<213> ORGANISM: Xanthomonas oryzae

<400> SEQUENCE: 2

Met Pro Val Ser Arg Tyr Ala Val Phe Gly His Pro Val Ala His Ser
1 5 10 15

Leu Ser Pro Ala Ile His Ala Asp Phe Gly Lys Gln Thr Gly Ile Val
20 25 30

Leu Asp Tyr Thr Ala Ile Asp Ala Pro Pro Glu Asp Phe Ser Ala Ala
35 40 45

Leu Gln Arg Phe Ala Asp Gly Gly Gly Lys Gly Ala Asn Val Thr Leu
50 55 60

Pro Leu Lys Glu Ala Ala Cys Ala Leu Ala Ser Ser Leu Ser Asp Arg
65 70 75 80

Ala Arg Leu Ala Gly Ala Val Asn Thr Leu Val Arg His Glu Gly Gln
85 90 95

Trp Gln Gly Glu Asn Thr Asp Gly Ile Gly Leu Val Arg Asp Leu Thr
100 105 110

Asp Arg His Gly Leu Asp Leu Arg Gly Arg Arg Val Leu Leu Leu Gly
115 120 125

Ala Gly Gly Ala Ala Arg Gly Val Ala Pro Ala Leu Leu Gln Ala Gly
```

-continued

```
            130                 135                 140
Ile Thr Glu Met Val Val Asn Arg Ser Pro Glu Arg Ala Asp Ala
145                 150                 155                 160

Leu Cys Asp Thr Leu Gly Glu Pro Gly Arg Val Val Ser Arg Tyr Ile
            165                 170                 175

Glu Asp Leu Arg Asp Leu Gly Asp Phe Glu Leu Ile Val Asn Ala Thr
            180                 185                 190

Ala Ala Gly Arg Asp Arg Asp Ala Gly Ala Phe Ala Met Pro Leu Gly
            195                 200                 205

Leu Val Asn Ser Leu Thr Ala Ala Val Asp Leu Asn Tyr Gly Ala Thr
            210                 215                 220

Ala Ile Ala Phe Leu Ala Trp Ala Arg Ser Ala Gln Cys Arg Tyr Ala
225                 230                 235                 240

Ile Asp Gly Leu Gly Met Leu Val Glu His Ala Ala Glu Ser Phe Ala
                245                 250                 255

Leu Trp His Gly Val Arg Pro Asp Thr Asp Pro Val Tyr Ala Ala Leu
            260                 265                 270

Arg Ala Arg Glu Ala Val Leu Val Ser Ala Asp
            275                 280
```